(12) United States Patent
Broyles et al.

(10) Patent No.: US 9,737,378 B2
(45) Date of Patent: Aug. 22, 2017

(54) DEVICE FOR DISPENSING A DENTAL MATERIAL

(71) Applicant: 3M INNOVATIVE PROPERTIES COMPANY, St. Paul, MN (US)

(72) Inventors: Bruce R. Broyles, Oakdale, MN (US); Christopher J. Claypool, Woodbury, MN (US); Marc Peuker, Schoendorf (DE); Greg E. Schrank, Bloomington, MN (US)

( * ) Notice: Subject to any disclaimer, the term of this patent is extended or adjusted under 35 U.S.C. 154(b) by 0 days.

(21) Appl. No.: 14/904,839

(22) PCT Filed: Jul. 24, 2014

(86) PCT No.: PCT/US2014/048011
§ 371 (c)(1),
(2) Date: Jan. 13, 2016

(87) PCT Pub. No.: WO2015/017245
PCT Pub. Date: Feb. 5, 2015

(65) Prior Publication Data
US 2016/0166356 A1    Jun. 16, 2016

(30) Foreign Application Priority Data
Jul. 31, 2013 (EP) .................................. 13178652

(51) Int. Cl.
*A61C 5/62* (2017.01)
*A61C 1/16* (2006.01)

(52) U.S. Cl.
CPC . *A61C 5/62* (2017.02); *A61C 1/16* (2013.01)

(58) Field of Classification Search
CPC ........... A61C 5/062–5/064; A61C 1/16; A61C 9/0026; A61M 5/24; A61M 5/1785; A61N 2/00

(Continued)

(56) References Cited

U.S. PATENT DOCUMENTS 3,339,810 A * 9/1967 Block ................ B65D 83/0011
                                                                 222/387
4,391,590 A * 7/1983 Dougherty ............. A61C 5/062
                                                                 433/90
(Continued)

FOREIGN PATENT DOCUMENTS

DE    EP 1543795 A1 * 6/2005    ............. A61C 5/062
DE    202006009628 U1 * 10/2007    ............. A61C 5/062
(Continued)

OTHER PUBLICATIONS

International Search Report for PCT International Application No. PCT/US2014/048011, mailed on Sep. 17, 2014, 3pgs.

*Primary Examiner* — Cris L Rodriguez
*Assistant Examiner* — Shannel Wright

(57) ABSTRACT

A device for dispensing a dental material has a cartridge with a dispensing end. The dispensing end has a dispensing opening for the dental material. The dispensing end further has in essence an axially symmetric shape with a truncation. The truncation provides the dispensing end with a generally flat dispensing surface through which the dispensing opening extends. The device has further a cap received on the dispensing end. The cap and the dispensing end are rotatable relative to each other between an open position, in which an orifice in the cap uncovers the dispensing surface, and a closed position, in which a closed space is formed between the cap and the dispensing surface. The device allows for a relatively convenient dispensation of dental material, in particular for a dispensation of a dental composite filling material.

14 Claims, 3 Drawing Sheets

(58) Field of Classification Search
USPC ........ 222/390; 604/232, 233, 235; 600/5, 12
See application file for complete search history.

(56) References Cited

U.S. PATENT DOCUMENTS

| | | | |
|---|---|---|---|
| 4,569,662 A | | 2/1986 | Dragan |
| 5,893,714 A | * | 4/1999 | Arnold .................. A61O 5/062 |
| | | | 433/90 |
| D419,236 S | | 1/2000 | Carlson |
| 6,524,103 B1 | * | 2/2003 | Winkler ............ B05C 17/00593 |
| | | | 222/575 |
| 7,128,246 B2 | | 10/2006 | Raia |
| 2003/0212372 A1 | | 11/2003 | Bills |
| 2012/0064481 A1 | * | 3/2012 | Cannon .............. B65D 83/0011 |
| | | | 433/90 |
| 2012/0258424 A1 | * | 10/2012 | Falsafi .................. A61C 5/062 |
| | | | 433/90 |

FOREIGN PATENT DOCUMENTS

| | | | |
|---|---|---|---|
| DE | WO 2013016642 A2 * | 1/2013 | ........... A61C 9/0026 |
| WO | WO 2002-076323 | 10/2002 | |
| WO | WO 2006-108085 | 10/2006 | |
| WO | WO 2013-016642 | 1/2013 | |

* cited by examiner

DEVICE FOR DISPENSING A DENTAL MATERIAL

FIELD OF THE INVENTION

The invention relates to a device for dispensing a dental material, and in particular to a device which has a dispensing end and a cap which are rotatable relative to each other between an open position for dispensing and a closed position for storage of the dental material.

BACKGROUND ART

Dental composite filling materials typically contain a predominant amount of fillers, for example quartz, and a relatively small amount of a flowable monomer. Such composites typically further contain a photo initiator allowing the monomer to be polymerized through light energy. Therefore the dental composite filling materials may be applied in a cavity in a patient's tooth and light-cured after application in the patient's tooth.

Typically such dental composite filling materials exhibit a relatively high viscosity and therefore typically require high forces for dispensing from a dispensing device. A dispensing device for dispensing dental composite filling materials is for example disclosed in U.S. Pat. No. 7,128,246 B2. Such a device stores a portion of a dental composite filling material which can be extruded by displacing a piston within the device. The device can be coupled to a hand-held dispensing gun providing a relatively high force for displacing the piston via a hand operable leverage.

An alternative dispensing device for dental composite filling materials is disclosed in U.S. Design Pat. No. Des. 419,236. WO 2006/108085 A2 discloses a syringe delivery system for dispensing a highly viscous material through a syringe delivery opening. The system includes a syringe barrel having a delivery opening, a plunger including a threaded shaft that threadably engages the syringe barrel for selectively dispensing a viscous material through the delivery opening, and a plunger gripping member in gripping communication with the plunger that includes means for sealing the threaded shaft of the plunger so as to prevent contamination by foreign matter. The syringe has a sheath that covers the threaded shaft of the plunger so as to hide the plunger beneath the sheath. The sheath provides a sealed environment for the threaded shaft so as to prevent entrance or contamination by foreign matter.

Although a variety of dispensers for dental composite filling materials are available there is still a need for a dispenser which is easy to use, which accounts for hygiene requirements in dentistry and which helps maximizing shelf life of the dental material stored therein.

SUMMARY OF THE INVENTION

The invention relates to a device for dispensing a dental material, and in particular for dispensing a dental composite filling material. The device comprises a cartridge having a dispensing end which extends along a longitudinal axis. The dispensing end has or provides a dispensing opening for the dental material, and has in essence an axially symmetric shape about the longitudinal axis. The axially symmetric shape has a truncation. The truncation provides the dispensing end with a generally flat dispensing surface through which the dispensing opening extends.

The term "truncation" as referred to in this specification is used to define the structural shape of the dispensing end. In particular the truncation provides a structure that is asymmetric with respect to or within an otherwise overall axially symmetric shape. The term "truncation" however does not limit the invention to any structure—although it covers such structure—which is actually obtained by a truncation action, for example by cutting, but refers to the structure as such independent from the method by which that structure was obtained.

The dispensing surface is oriented in a non-orthogonal relationship with the longitudinal axis. In particular the three-dimensional shape of the dispensing surface may in at least one dimension be oriented at an inclination angle which non-parallel as well as different from 90 degrees relative to the longitudinal axis. The device further comprises a cap disposed over, or received on the dispensing end. The cap and the dispensing end are rotatable relative to each other about the longitudinal axis between an open position and a closed position. In the open position an orifice in the cap uncovers the dispensing surface, whereas in the closed position a closed space is formed between the cap and the dispensing surface. In the closed position the cap thus preferably seals the dispensing opening from the exterior of the device although the closed space is present between the cap and the dispensing surface.

The invention is advantageous in that it provides a device which is relatively easy to use. Further the device preferably allows for dispensation of a portion of a dental material and for encapsulating that portion within the device from the exterior of the device. Further the device preferably allows for picking up one or more sub-portion of the dispensed portion and for keeping any remainder of the dispensed portion encapsulated in the device. Thus the device may help maximizing the time period over which the dental material can be used after dispensation from the cartridge. The device further helps metering a portion of dental material dispensed from the device and allows the dental material to be picked-up in a relative convenient manner.

In one embodiment the dispensing surface is generally planar. Although the dispensing surface may be planar or exactly planar it has been found that a slight convex shape of the dispensing surface may allow for picking up a portion of dental material dispensed from the dispensing opening relatively conveniently by a dental instrument, for example a spatula. This is during manually cutting off the dental material adjacent the dispensing opening the dispensing surface may provide for guidance of the spatula and the curvature of the slight convex shape may allow slight skewing of the spatula as it may occur during such manual operation. Further the dispensing surface preferably entirely surrounds the dispensing opening. Thus the dispensing surface may allow for guiding the dental instrument relative reliable and precisely over the dispensing opening.

In one embodiment the axially symmetric shape is generally cylindrical. The symmetric shape may particularly be formed by a generally cylindrical outer side face 14, a free front face 15 and the dispensing surface. The dispensing surface preferably forms a first edge 16 with the side face 14 and a second edge 17 with the front face 15. The skilled person will recognize that a conical shape may be used instead of a cylindrical shape as appropriate. The first and second edges 16, 17 may form a common continuous edge with one another.

In a further embodiment the front face 15 of the dispensing end comprises a generally ball-shaped surface 16. The front face 15 of the dispensing end 111 may however alternatively be planar or generally planar. The front face of the dispensing end may further have a radius 18 in the transition between the front face 15 and the side face 14. The front face may be formed by a ball-shaped front wall which further has a ball-shaped inner face 19, optionally with a radius 18 in the transition between the inner face 15 and inner side faces 14. A so shaped front wall may help maximizing the resistance of the cartridge to pressure exerted to the front wall during dispensation of the dental material.

In one embodiment the dispensing surface and the longitudinal axis are inclined with respect to each other in an angle of between about 30 degrees and 60 degrees. Accordingly the dispensing surface may extend along essentially two dimensions, one of which is inclined with respect to the longitudinal axis in an angle of between about 30 degrees and 60 degrees, preferably in an angle of about 45 degrees. The angle thereby refers to the included angle between the dispensing surface and the longitudinal axis, measured within boundaries of the device.

In a further embodiment the cartridge has a substantially lightproof cartridge wall at least for visible light. For the purpose of the present specification "visible light" refers to light at wavelengths of between 380 nm (nanometers) and 750 nm. The cartridge may particularly have a lightproof or substantially lightproof cartridge wall for blue light which for the purpose of the present specification refers to light at wavelengths of between 450 nm and 495 nm. Accordingly the cartridge may be adapted to block light which would be suitable to initiate hardening of a light-hardenable dental material. At least the dispensing end of the device may be formed by the lightproof cartridge wall. Further the cap may have a lightproof or substantially lightproof cap wall at least for visible light or in more particular for blue light. Thus also the cap may be adapted to block light which is suitable to initiate hardening of a light-hardenable dental material. Therefore the device is preferably overall adapted to prevent a light-hardenable dental material from exposure to light, and thus to prevent premature hardening of the dental material within the device.

In one embodiment the cap and the cartridge are locked with one another against separation. For example the cap may have one or more retainer or an annular bulge at its lateral inner surface, and the dispensing end may have a corresponding groove for engaging with the retainer or bulge. The groove may be located behind the front most free end of the dispensing end. The skilled person will recognize a variety of solutions to retain the cap and the dispensing end by irreversible snap fits, interlock mechanisms or bondings.

In a preferred embodiment the cartridge forms a chamber for storing the dental material. The device further preferably comprises a plunger for extruding the dental material from the chamber. The device may comprise a threaded plunger. The device thus may be adapted such that the dental material is extrudable by rotation of the plunger. Such a threaded plunger may be advantageous for extruding a dental material having a high viscosity, because the threaded plunger typically converts a relatively low operation force (applied by a user) into a relatively high extrusion force. Further such a threaded plunger typically allows the dental material to be dispensed relatively accurately. The skilled person will however recognize that a push plunger may be likewise used with the present invention, for example for extruding comparably low viscous materials. In one embodiment the device, in particular the cartridge, comprises or contains the dental material, and in particular a dental composite filling material. The dental composite filling material is preferably a light-hardenable dental composite filling material. The dental material may be a dental composite material comprising a predominant portion by weight of fillers, a hardenable monomer and a photo initiator adapted for initiating hardening of the monomer.

In more particular the dental composite filling materials may be characterized by at least one or all of the following features:

a) radiation curable (especially within the region of visible light, in particular blue light);
b) formulated as a one-component composition (in contrast to e.g. dental impression materials which are formulated as two-component compositions which are mixed from a base paste and a catalyst paste shortly prior to use);
c) highly viscous;
d) slightly tacky, for example sticky if touched with the fingers;
e) "cuttable", for example can be cut into pieces with a dental instrument or knife (scalpel);
f) "firm" for example shapeable by applying manual forces but generally self-supporting in absence of such forces at least over a time period of about 5 minutes.

A combination of the features (a), (b), (c) and (d) is sometimes preferred.

Dental composite materials typically comprise a hardenable resin matrix comprising hardenable components, an initiator system suitable to harden the hardenable components contained in the resin matrix and filler(s). The filler content is typically above about 50, 60 or 70 wt.-% with respect to the weight of the dental composite material. Typical ranges include from about 50 to about 90 wt.-% or from about 60 to about 80 wt.-%. The hardenable components typically comprise unsaturated moieties (carbon-carbon unsaturation) like (meth)acrylate moieties. In order to be crosslinkable, the hardenable components typically comprise at least about 2 unsaturated moieties.

The composite material may comprise only one type of filler or different types of fillers. Suitable filler(s) include fumed silica, quartz, ground glasses, non-water-soluble fluorides such as $CaF_2$, silica gels such as silicic acid, in particular pyrogenic silicic acid and granulates thereof, cristobalite, calcium silicate, zirconium silicate, zeolites, including the molecular sieves, barium sulphate and/or yttrium fluoride. Suitable fumed silicas include for example, products sold under the tradename Aerosil™ series OX-50, -130, -150, and -200, Aerosil R8200 available from Degussa AG, (Hanau, Germany), CAB-O-SIL™ M5 available from Cabot Corp (Tuscola, Ill.), and HDK types, e.g. HDK-H 2000, HDK H15; HDK H18, HDK H20 and HDK H30 available from Wacker. The average surface area of the silica particles is preferably greater than about 15 $m^2/g$ more preferably greater than about 30 $m^2/g$.

A "hardenable component or material" or "polymerizable component" is any component which can be cured or solidified e.g. by radiation-induced polymerization. A hardenable component may contain only one, two, three or more polymerizable groups. Typical examples of polymerizable groups include unsaturated carbon groups, such as a vinyl group being present i.a. in a (methyl)acrylate group.

"(Meth)acryl" is a shorthand term referring to "acryl" and/or "methacryl". For example, a "(meth) acryloxy" group is a shorthand term referring to either an acryloxy group (i.e., CH2=CH—C(O)—O—) and/or a methacryloxy group (i.e., CH2=C(CH3)-C(O)—O—).

A "curing, hardening or setting reaction" is used interchangeable and refers to a reaction wherein physical properties such as viscosity and hardness of a composition changes over the time due to a chemical reaction between the individual components.

"Light hardenable" shall mean that the composition can be cured by applying radiation with light, preferably radiation with light at a wavelength within the visible light spectrum under ambient conditions (for example approximately 23±10 degrees Celsius) and within a reasonable time frame (e.g. within about 15, 10 or 5 minutes).

In one embodiment the cap comprises an indicator which indicates a tooth color associated with the color of the dental composite material. For example the color of the dental composite material may have a color according to the VITA color scheme or shade guide. The VITA shade guide provides certain predetermined tooth color shades indicated by a encoding, for example the encodings B1, A1, B2, D2, A2, C1, C2, D4, A3, D3, B3, A3.5, B4, C3, A4, C4, each being representative of a certain tooth color. Accordingly a user of the device may easily and quickly identify the appropriate color of the dental material via the color of the cap.

In a further embodiment a kit of devices is provided, the kit comprising a plurality of devices containing differently colored dental materials. For example the kit may comprise one or more devices containing a first color, one or more devices containing a second color, and one or more devices containing further colors.

The indicator may comprise an encoding providing the tooth color as plain text (for example B1, A1, B2, D2, A2, C1, C2, D4, A3, D3, B3, A3.5, B4, C3, A4, C4). Further the indicator may comprise a false color code indicating a certain tooth color. Such false color preferably significantly distinguishes from a tooth color. Further different tooth colors are preferably represented by significantly distinguishing false colors, for example A1 and A2 by red and green, respectively. Thus a certain tooth color may be easily and quickly identified in a kit of devices containing different tooth colors.

DETAILED DESCRIPTION OF THE INVENTION

Figure 1:
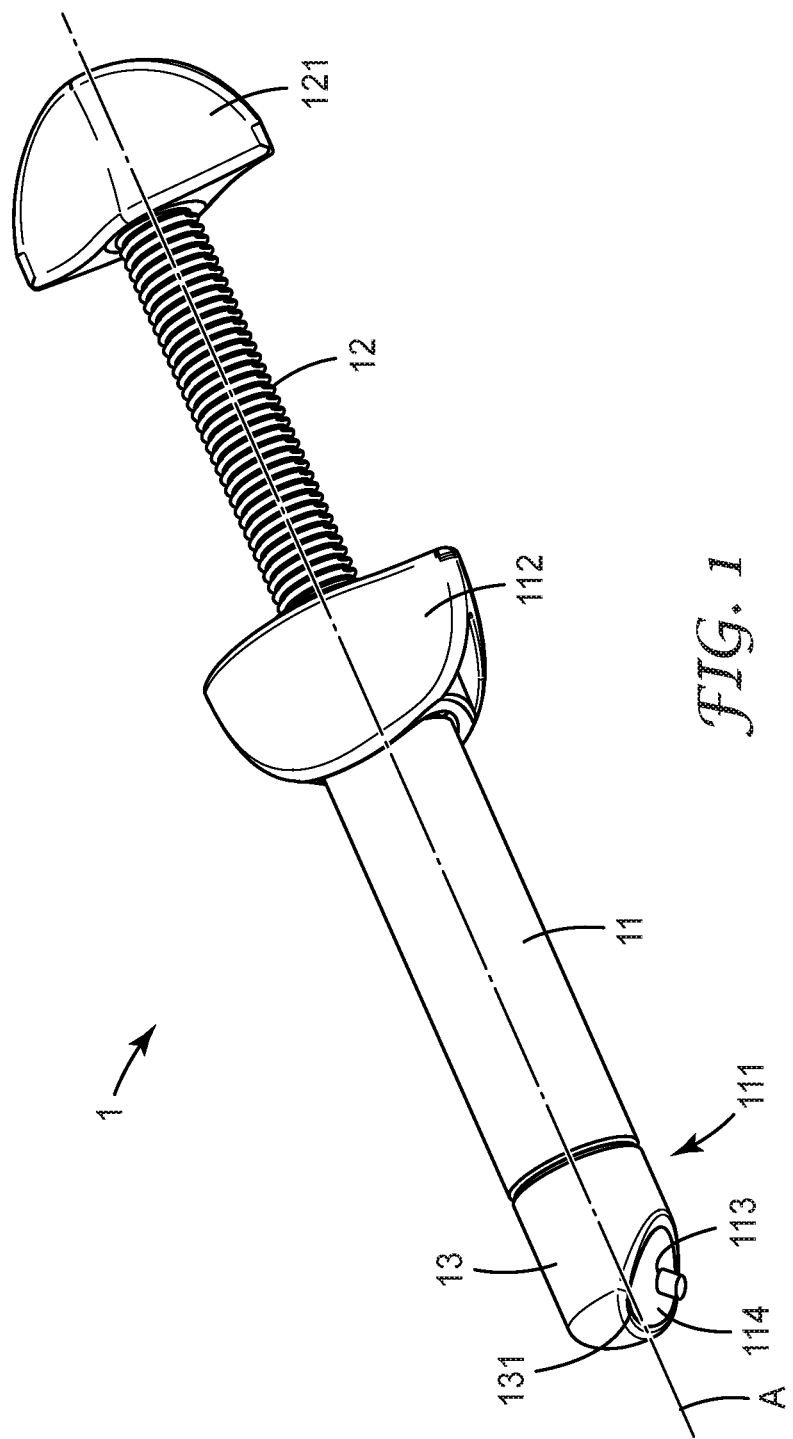
FIG. 1 is a perspective view of a device according to an embodiment of the invention.

FIG. 1 shows a device 1 for dispensing a dental material. The device 1 comprises a cartridge 11, a threaded plunger 12 and a cap 13. The cartridge 11 preferably contains a dental material, in particular a dental composite filling material. The device 1, the cartridge 11 and the threaded plunger 12, extend generally straight along a longitudinal axis A. A front end of the cartridge 11 forms a dispensing end 111 (in the Figure partially covered by the cap 13) which has a dispensing opening 113 for the dental material. The dispensing opening 113 in the Figure is visible through an orifice 131 in the cap 13.

The threaded plunger 12 is received with its front end within the rear end of the cartridge 11. The threaded plunger 12 and the cartridge 11 are rotatable relative to each other about the longitudinal axis A for advancing the dental material toward the dispensing end 111. Further a rear end of the threaded plunger 12 and the rear end of the cartridge 11 each have actuation wings 112, 121, respectively, allowing a user to rotate the threaded plunger 12 and the cartridge 11 relative to each other, and for dispensing the dental material. The skilled person will appreciate that other actuation means may be provided instead or in addition to the actuation wings. Examples of such actuation means include actuation knobs, actuation wheels, actuation levers or any other appropriate structures.

Figure 2:
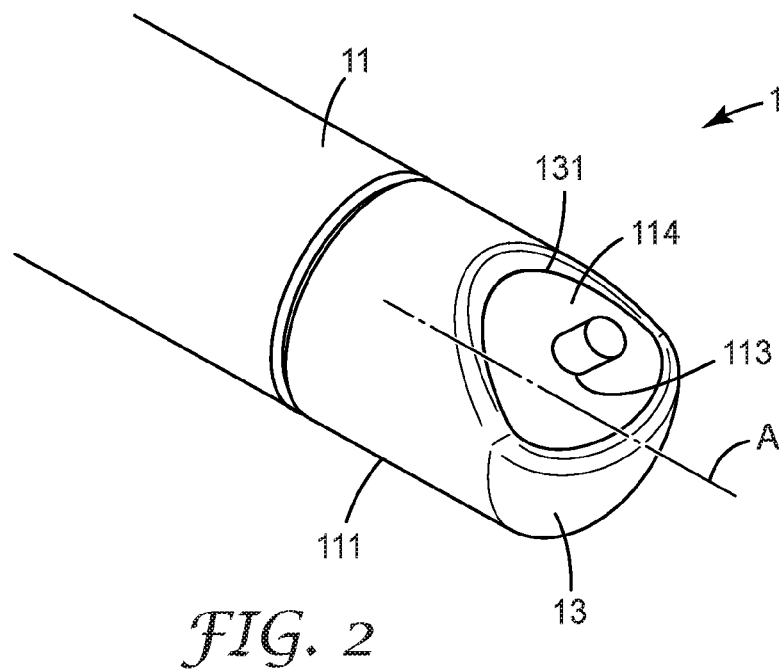
FIG. 2 is a partial perspective view of a device according to an embodiment of the invention in an open position.

FIG. 2 shows the dispensing end 111 of the device 1 in an enlarged view. The dispensing end 111 has about the longitudinal axis A an essentially cylindrical shape with an inclined truncation. In particular the longitudinal axis A forms the cylinder axis of the essentially cylindrical shape of the dispensing end 111 and the truncation provides the dispensing end with a generally flat dispensing surface 114 that is inclined with respect to the longitudinal axis A. More generally therefore the dispensing end 111 has in essence an axially symmetric shape about the longitudinal axis with a truncation that provides the dispensing end with a generally flat dispensing surface 114. The dispensing opening 113 extends through this dispensing surface 114.

The dispensing surface 114, although it may be slightly curved, preferably in essence approximates a plane, or the dispensing surface may be generally or exactly planar. At least one of the two dimensions of the plane which the dispensing surface 114 is based on is inclined with respect to the longitudinal axis A. This means that the at least one dimension is neither orthogonal to the longitudinal axis nor parallel or congruent with longitudinal axis. In contrast the at least one dimension preferably forms an (included) angle with the longitudinal angle of between about 30 degrees to 60 degrees. It has been found that such a configuration allows a user of the device to pick up dental material dispensed from the device 1 relatively conveniently, particularly if a spatula is used for striping off a portion of the dental material protruding from the dispensing opening 113. The dispensing surface 114 thereby helps guiding the spatula such that the portion of dental material can be separated directly adjacent dispensing opening 113 so that generally no extruded dental material resides outside the opening of the device. Thus also the accuracy of the amount of dental material obtainable from the device 1 may be maximized.

The device 1 is adapted such that the cap 13 and the dispensing end 111 are rotatable relative to each other about the longitudinal axis. In particular the cap 13 and the dispensing end 111 are rotatable between an open position (shown in FIG. 2), in which the orifice 131 in the cap uncovers the dispensing surface 114, and a closed position.

Figure 3:
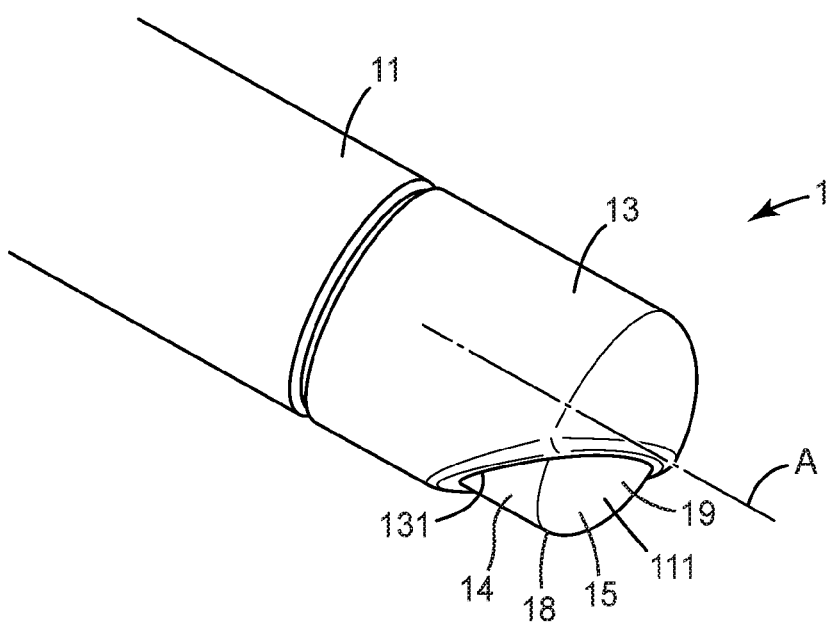
FIG. 3 is a partial perspective view of the device shown in FIG. 2 in a closed position.

The device 1 is shown in its closed position in FIG. 3. With respect to the situation shown in FIG. 2 the cap 13 in FIG. 3 is rotated by 180 degrees relative to the cartridge 11. In the closed position a portion of the dispensing end 111 seals the orifice 131 of the cap and the dispensing surface as well as the dispensing opening (neither being visible in this view) are covered and preferably sealed by the cap 13. In the example a portion of the dispensing end 111 extends through the orifice 131 and thus seals the orifice 131.

Further in the closed position of the device 1 a closed space is formed between the cap 13 and the dispensing surface 114. This is visualized in FIG. 4 which illustrates a situation in which the cap 13 and the cartridge 11 are positioned in an intermediate position between the open and the closed position.

Figure 4:
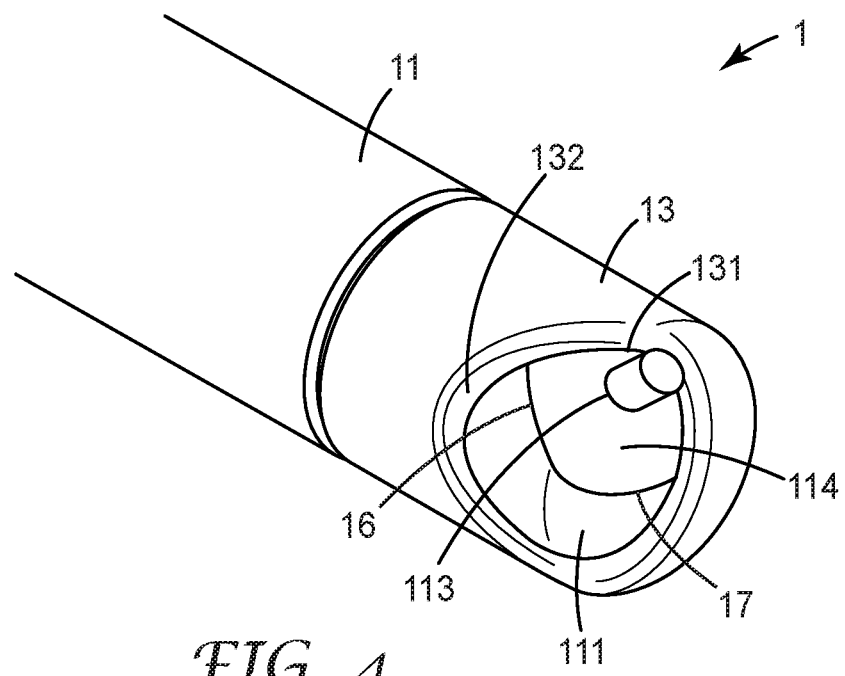
FIG. 4 is a partial perspective view of the device shown in FIG. 2 positioned in an intermediate position between the open and the closed position.

FIG. 4 illustrates that due to the shape of the dispensing end 111 and the shape of the cap 13 a space is formed between the cap 13 and the dispensing surface 114 in positions outside the open position. In the closed position that space is closed and preferably sealed, preferably hermetically sealed.

As shown, the cap 13 is generally cup-shaped and has an essentially cylindrical inner shape which is sized to snugly fit onto the generally cylindrical shape of the dispensing end 111. The cap 13 further has a truncation which provides the cap 13 with the orifice 131. The truncation further preferably provides the cap 13 with a generally flat orifice region 132 which with the dispensing surface 114 forms one contiguous area in the open position (shown in FIG. 2) of the device 1. Accordingly the cap 13 preferably does not inhibit any removal of the dental material dispensed from the dispensing opening 113, for example by use of a spatula.

In contrast in the closed position (shown in FIG. 3) the cap 13 entirely covers the dispensing surface 114 with the dispensing opening 113. The shapes of the dispensing end 111 and the cap 13 are such that in the closed position of the device 1 the inner portion of the cap 13 in combination with the dispensing surface 114 forms a hollow closed space. This space may be used to (for example temporarily) accommodate a portion of dental material dispensed from the dispensing opening therein until use, for example by a dentist. Accordingly the device 1 allows pre-dispensing a portion of dental material and storing the pre-dispensed portion in the space between the cap 13 and the dispensing surface 111. In a dentist's practice therefore a dentist's assistant may pre-dispense a portion of the dental material and keep the pre-dispensed portion stored within the device 1. During storage the portion of dental material is preferably isolated within the device 1 from the environment and thus protected against unintentional drying and/or against exposure to light. Latter may be particularly advantageous for use of the device 1 with light-hardenable dental materials, like light-hardenable dental composite filling materials, if the device is adapted to block light from entering into the space. The cap 13 and the cartridge 11 therefore may be made of a light-blocking or opaque material, for example a plastic material comprising opaque fillers, a metal (for example aluminum) coating or any other material having an appropriate light-blocking configuration.

Figure 5:
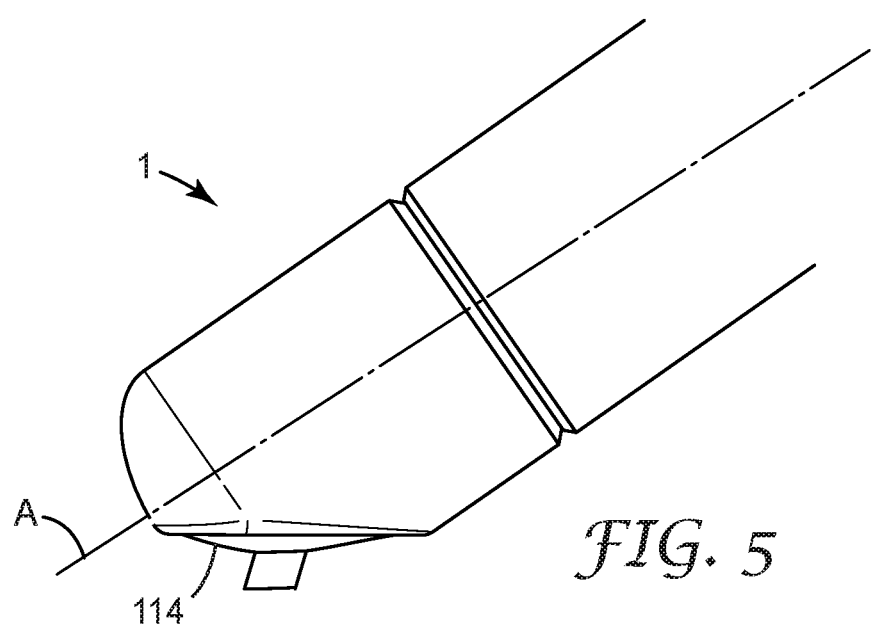
FIG. 5 is a partial perspective view of the device shown in FIG. 2 in use for dispensing on a surface.

FIG. 5 illustrates a use of the device 1 for dispensing a portion of dental material directly on a surface, for example onto a dental pad from which the material may be picked up by a dental instrument. Accordingly the device provides several modes of use, for example the pre-dispensing and storing of a portion of dental material, a use with a dental instrument, like a spatula, or a use for dispensing on a surface, like a dental pad. Therefore the device 1 helps facilitating the preparation of the dental material in a dental treatment and thus may help reducing efforts and costs in a dental practice.

The invention claimed is:

1. A device for dispensing a dental material comprising:
   a cartridge having a dispensing end extending along a longitudinal axis;
   the dispensing end having a dispensing opening for the dental material;
   the dispensing end having generally an axially symmetric shape about the longitudinal axis, wherein the axially symmetric shape has a truncation;
   the truncation providing the dispensing end with a generally flat dispensing surface through which the dispensing opening extends;
   the dispensing surface being oriented in a non-orthogonal relationship with the longitudinal axis;
   the device further comprising a cap disposed over the dispensing end;
   the cap and the dispensing end being rotatable relative to each other about the longitudinal axis between an open position, in which an orifice in the cap uncovers the dispensing surface, and a closed position, in which a closed space is formed between the cap and the dispensing surface.

2. The device of claim 1, wherein the dispensing surface is generally planar, and wherein the dispensing surface entirely surrounds the dispensing opening.

3. The device of claim 1, wherein the axially symmetric shape is generally cylindrical formed by a generally cylindrical outer side face, a free front face and the dispensing surface, wherein the dispensing surface forms a first edge with the side face and a second edge with the front face.

4. The device of claim 3, wherein the first and second edges form a common continuous edge with one another.

5. The device of claim 3, wherein the front face of the dispensing end comprises a generally ball shaped surface and optionally a radius in the transition between the front face and the side face.

6. The device of claim 1, wherein the dispensing surface and the longitudinal axis are inclined with respect to each other in an angle of between about 30 degrees and 60 degrees.

7. The device of claim 1, wherein the cartridge has a substantially lightproof cartridge wall at least for visible light in at wavelengths of between 380 nanometers and 750 nanometers.

8. The device of claim 7 wherein, at least the dispensing end is formed by the lightproof cartridge wall, and wherein further the cap has a substantially lightproof cap wall at least for visible light.

9. The device of claim 1, wherein the cap and the cartridge are locked with one another against separation.

10. The device of claim 1, wherein the cartridge forms a chamber for storing the dental material, and further comprising a plunger for extruding the dental material from the chamber.

11. The device of claim 10, comprising a threaded plunger, wherein the device is adapted such that the dental material is extrudable by rotation of the plunger.

12. The device of claim 1, comprising the dental material.

13. The device of claim 12, wherein the dental material is a dental composite material comprising a predominant portion by weight of fillers, a hardenable monomer and a photo initiator adapted for initiating hardening of the monomer.

14. The device of claim 13, wherein the cap comprises an indicator which indicates a tooth color associated with the color of the dental composite material.

* * * * *